US008116531B2

(12) United States Patent
Kanda

(10) Patent No.: US 8,116,531 B2
(45) Date of Patent: Feb. 14, 2012

(54) IMAGE PROCESSING APPARATUS, IMAGE PROCESSING METHOD, AND IMAGE PROCESSING PROGRAM PRODUCT

(75) Inventor: Yamato Kanda, Hino (JP)

(73) Assignee: Olympus Corporation, Tokyo (JP)

( * ) Notice: Subject to any disclaimer, the term of this patent is extended or adjusted under 35 U.S.C. 154(b) by 699 days.

(21) Appl. No.: 12/277,775

(22) Filed: Nov. 25, 2008

(65) Prior Publication Data

US 2009/0148014 A1 Jun. 11, 2009

Related U.S. Application Data

(63) Continuation of application No. PCT/JP2007/057924, filed on Apr. 10, 2007.

(30) Foreign Application Priority Data

May 26, 2006 (JP) ................................. 2006-147316

(51) Int. Cl.
G06K 9/00 (2006.01)
A61B 5/05 (2006.01)

(52) U.S. Cl. .......................... 382/107; 382/274; 600/425

(58) Field of Classification Search .................. 382/100, 382/103, 106, 107, 108, 128–133, 162, 165, 382/168, 173, 181, 194, 224, 232, 254, 274, 382/276, 287–295, 305, 312; 600/109, 425, 600/439; 356/442; 378/4, 21

See application file for complete search history.

(56) References Cited

U.S. PATENT DOCUMENTS

| 5,566,249 A * | 10/1996 | Rosenlof et al. .............. 382/257 |
| 5,835,620 A * | 11/1998 | Kaplan et al. ................. 382/133 |
| 6,727,990 B1 * | 4/2004 | Niemi ............................ 356/442 |
| 7,676,257 B2 * | 3/2010 | Suryanarayanan et al. .. 600/425 |
| 7,742,629 B2 * | 6/2010 | Zarkh et al. .................... 382/128 |
| 7,824,336 B2 * | 11/2010 | Kawabata et al. ............. 600/439 |
| 2007/0191677 A1 * | 8/2007 | Nishimura et al. ............ 600/109 |

FOREIGN PATENT DOCUMENTS

| JP | 10-508709 | 8/1998 |
| JP | 2004-337596 | 12/2004 |
| JP | 2004-354100 | 12/2004 |
| JP | 2005-192880 | 7/2005 |
| JP | 2006-122502 | 5/2006 |
| WO | WO 02/094098 A1 | 11/2002 |
| WO | WO 2005/101314 A2 | 10/2005 |

OTHER PUBLICATIONS

Takagi M., et al. "Shinpen Gazo Kaiseki Handbook", Sep. 10, 2004, pp. 1669-1672, University of Tokyo Press, (partial English translation).

Chen D. et al., "Template-based bubble identification and tracking in image sequences", International Journal of Thermal Sciences, Mar. 2006, pp. 321-330, vol. 45.

Extended Supplementary European Search Report dated Feb. 8, 2010.

E.R: Davies: "Machine Vision: Theory, Algorithms, Practicalities", 2005, Morgan Kaufman—Elsevier, pp. 141-143 and 232-248, XP002564427.

* cited by examiner

*Primary Examiner* — Seyed Azarian

(74) *Attorney, Agent, or Firm* — Scully, Scott, Murphy & Presser, P.C.

(57) ABSTRACT

An image processing apparatus includes an edge intensity calculator which calculates an edge intensity of a pixel in an image; and a correlation value calculator which calculates a correlation value between the calculated edge intensity and a bubble model set in advance based on characteristics of a bubble image. The apparatus also includes a bubble area detector which detects a bubble area based on the calculated correlation value.

19 Claims, 14 Drawing Sheets

IMAGE PROCESSING APPARATUS 100
INTRA-CAVITY IMAGE

- 120 MEMORY
- 110 CALCULATION UNIT
  - 101 EDGE INTENSITY CALCULATOR
  - 102 CORRELATION VALUE CALCULATOR
  - 103 BUBBLE AREA DETECTOR

BUBBLE AREA INFORMATION

IMAGE OF BUBBLE PART

CHANGE IN PIXEL VALUE ALONG LINE A-A'

CONVEX EDGE OF INSIDE OF BUBBLE DUE TO ILLUMINATION REFLECTION

CONVEX EDGE OF BUBBLE CONTOUR

133 ↗   134

136a  136b

135

→ : GRADIENT DIRECTION OF CONCENTRATION IN EACH PIXEL ALONG PATH

US 8,116,531 B2

IMAGE PROCESSING APPARATUS, IMAGE PROCESSING METHOD, AND IMAGE PROCESSING PROGRAM PRODUCT

CROSS-REFERENCE TO RELATED APPLICATIONS

This application is a continuation of PCT international application Ser. No. PCT/JP2007/057924 filed on Apr. 10, 2007 which designates the United States, incorporated herein by reference, and which claims the benefit of priority from Japanese Patent Applications No. 2006-147316, filed on May 26, 2006, incorporated herein by reference.

BACKGROUND OF THE INVENTION

1. Field of the Invention

The present invention relates to an image processing apparatus, an image processing method, and an image processing program product which detect a bubble area present in an image, and specifically to an image processing apparatus and an image processing program product which detect a bubble area present in an image captured in a body cavity.

2. Description of the Related Art Japanese Patent Application Laid-Open No. 2004-337596 discloses, as an image processing on an intra-cavity image, a processing of determining an organ based on average color information of an image captured by a capsule endoscope. Specifically, an average value of a red color level and an average value of a blue color level in a pixel of the image are calculated, a discoloration edge position whose amount of change in each color level is not less than a predetermined amount is detected after the calculated values are smoothed in a time-line direction, and a transition of organs is determined in each image among images which are captured by a capsule endoscope and loaded as time-series successive images.

Japanese Patent Application Laid-Open No. 2005-192880 discloses a processing of detecting a diseased site based on color information of each pixel in an image captured by a capsule endoscope. Specifically, each pixel or an averaged pixel value in the image is mapped onto a feature space based on the color information, a cluster for a normal mucous membrane and a cluster for a diseased site are specified after performing clustering in the feature space, and a pixel area classified as the diseased site cluster is detected as a diseased site.

However, since an air bubble (hereinafter simply referred to as "a bubble") is present in a body cavity captured by a capsule endoscope, it often happens that a bubble as well as a mucous membrane are captured in an intra-cavity image. When a bubble is present in an image, an average value, calculated in Japanese Patent Application Laid-Open No. 2004-337596, of each color level in the image is not a value which adequately reflects an original color level of the mucous membrane due to an influence of the bubble. Thus, an accuracy of an organ determination deteriorates.

Besides, a distribution of a pixel of a bubble area is very wide in the feature space based on the color information and overlaps a distribution of a normal mucous membrane and a diseased site. Therefore, when a detection of a diseased site is performed including pixel information of a bubble area, an accuracy of detection deteriorates in Japanese Patent Application Laid-Open No. 2005-192880, too.

In both of the above cases, as long as a bubble area can be detected in an intra-cavity image, a deterioration in accuracy of an organ determination and a diseased site detection can be suppressed by eliminating a pixel corresponding to the bubble area as an invalid pixel from a subsequent processing. However, the current situation is that no effective solution has been found out to deal with the problem of detecting a bubble area in an intra-cavity image so far.

SUMMARY OF THE INVENTION

An image processing apparatus according to an aspect of the present invention includes: an edge intensity calculator which calculates an edge intensity of a pixel in an image; a correlation value calculator which calculates a correlation value between the calculated edge intensity and a bubble model set in advance based on characteristics of a bubble image; and a bubble area detector which detects a bubble area based on the calculated correlation value.

An image processing program which makes an image processing apparatus execute a processing of detecting a bubble area in an image according to another aspect of the present invention, causes the image processing apparatus to execute: an edge intensity calculating procedure which calculates an edge intensity of a pixel in an image; a correlation value calculating procedure which calculates a correlation value between the calculated edge intensity and a bubble model set in advance based on characteristics of a bubble image; and a bubble area detecting procedure which detects a bubble area based on the calculated correlation value.

An image processing method according to still another aspect of the present invention includes calculating an edge intensity of a pixel in an image; calculating a correlation value between the calculated edge intensity and a bubble model set in advance based on characteristics of a bubble image; and detecting a bubble area based on the calculated correlation value.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2 shows an example of an intra-cavity image, including a bubble, captured by a capsule endoscope and the like;

DETAILED DESCRIPTION OF THE PREFERRED EMBODIMENTS

Exemplary embodiments of the present invention will be explained with reference to the accompanying drawings. In the exemplary embodiments of the present invention described below, an image processing apparatus which detects a bubble area in an intra-cavity image captured by a capsule endoscope and the like will be shown. An intra-cavity image captured by a capsule endoscope is normally a color image having a pixel level (a pixel value) for each of red (R), green (G), and blue (B) colors in each pixel position. However, an intra-cavity image in the embodiment is assumed to be a light-and-shade image, which is converted from such a color image as described above via a known conversion method, like an image expressed by a luminance (via an YCbCr conversion), a luminosity (via an HSI conversion), and the like. As for the conversion, though it is more preferable that image information of a bubble part is less lost, only the G component of the color image may be used to make the light-and-shade image since it is generally known that a change in color hue of an intra-cavity image normally depends most on an absorption spectrum (wavelength) of hemoglobin in blood in a case of not using a pigment, a stain, and the like and that structural information is mostly included in the G component.

Figure 1:
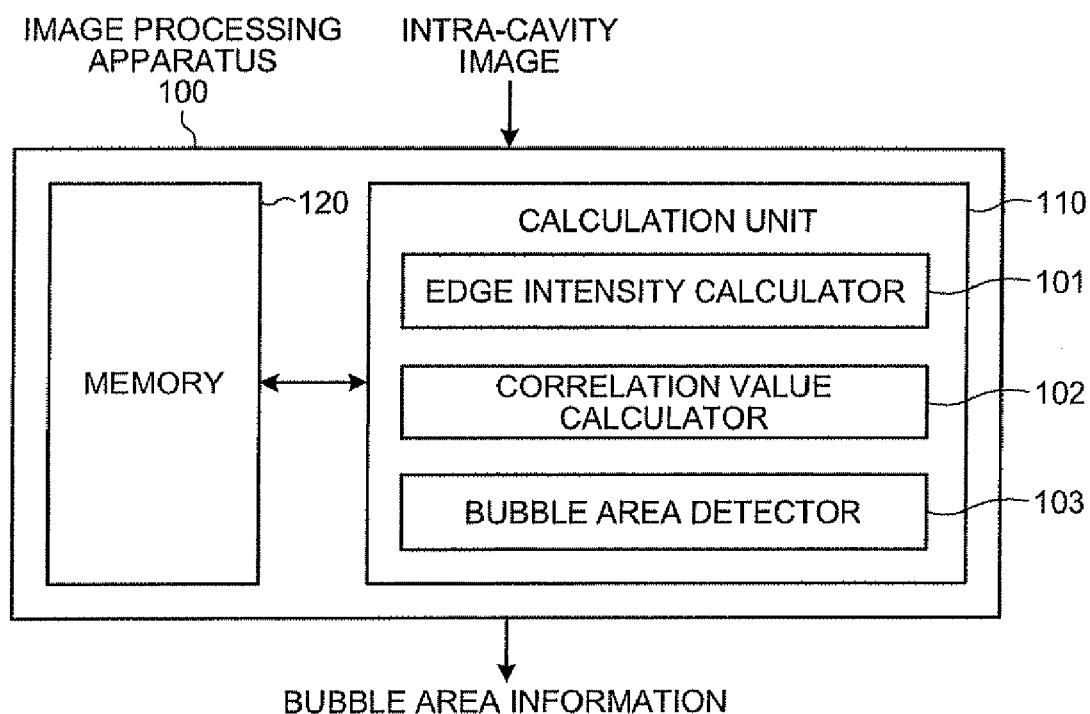
FIG. 1 is a schematic block diagram of a structure of an image processing apparatus according to a first embodiment of the present invention.
Figure 2:
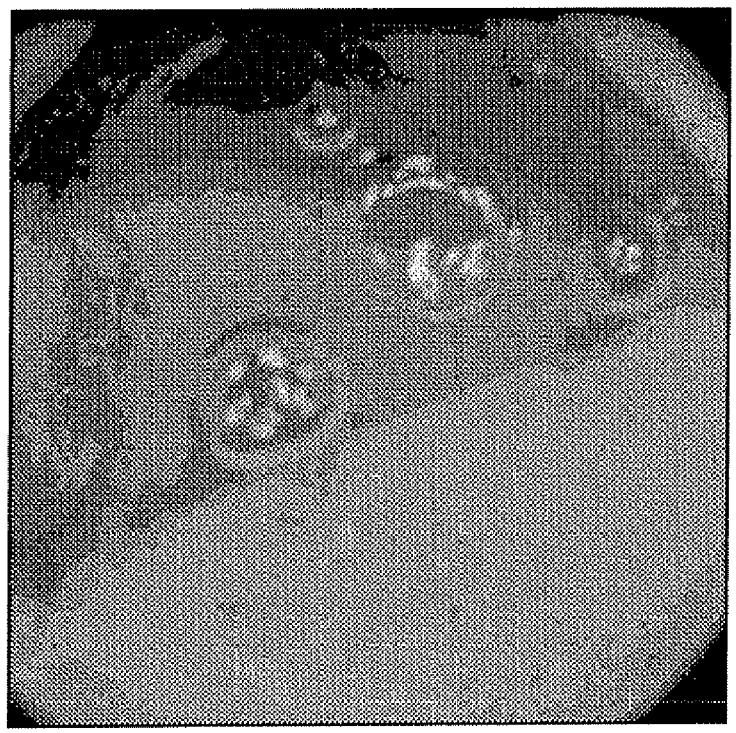

A first embodiment will be explained. FIG. 1 is a schematic block diagram of a structure of an image processing apparatus according to the first embodiment. FIG. 2 shows an example of an intra-cavity image, including a bubble, captured by a capsule endoscope and the like. An image processing apparatus 100 according to the first embodiment includes: a calculation unit 110 which is constructed by a microcomputer and has an edge intensity calculator 101 that calculates an edge intensity of a pixel in such an intra-cavity image obtained by imaging an inside of a body cavity as shown in FIG. 2, a correlation value calculator 102 that calculates a correlation value between the calculated edge intensity and a bubble model which is set in advance based on characteristics of a bubble image, and a bubble area detector 103 that detects a bubble area in the image based on the calculated correlation value; and a memory 120 which stores obtained intra-cavity images and data used by each part. As for a configuration for inputting intra-cavity images as a processing subject into the image processing apparatus 100 and a configuration for processing the result of the bubble area detection after the result is output, no specific limitation is set in the embodiment.

Figure 3:
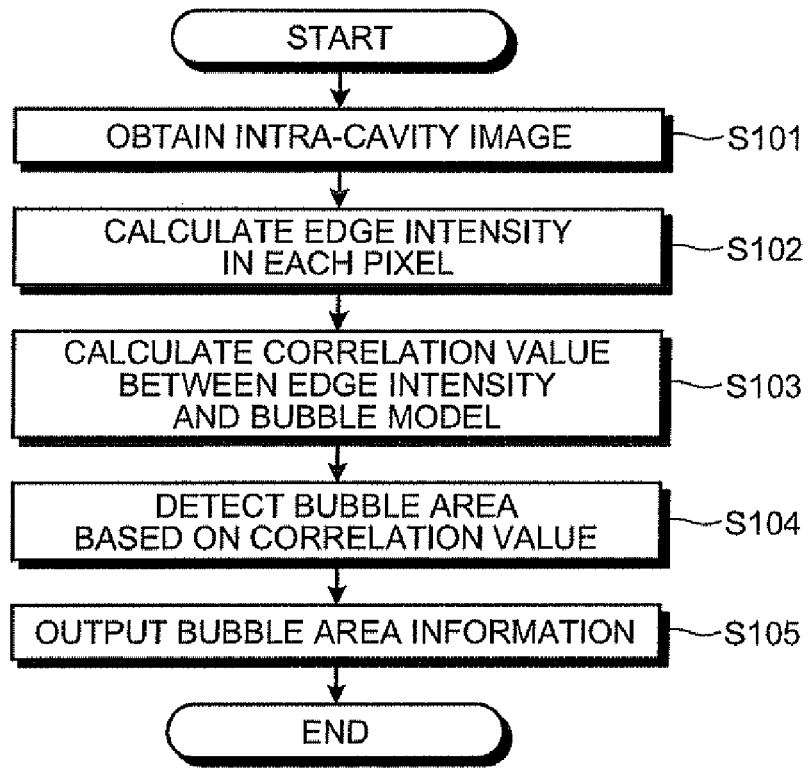
FIG. 3 is a schematic flowchart of a processing executed by a calculation unit of the image processing apparatus according to the first embodiment.

FIG. 3 is a schematic flowchart of a processing executed by the calculation unit 110 of the image processing apparatus 100 according to the first embodiment. An image processing procedure will be explained below in contrast with the structure shown in FIG. 1.

Figure 4:
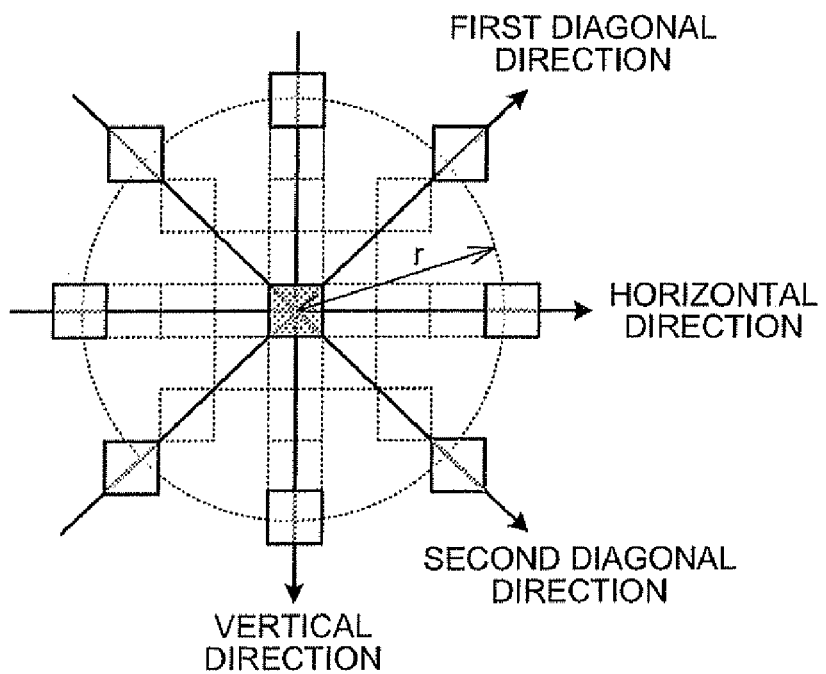
FIG. 4 is an explanatory view of directions of a quadratic differentiation calculation in an edge intensity calculation.

First of all, the calculation unit 110 obtains an intra-cavity image as a processing subject (step S101). Next, the edge intensity calculator 101 calculates an edge intensity of a pixel of the obtained intra-cavity image (step S102). While there are various methods for calculating the edge intensity, a method of using a processing of a quadratic differentiation for each direction will be explained here. FIG. 4 is an explanatory view of directions of a quadratic differentiation calculation in the edge intensity calculation. First, a quadratic differentiation in a horizontal direction dH, a quadratic differentiation in a vertical direction dV, a quadratic differentiation in a first diagonal direction dD1, and a quadratic differentiation in a second diagonal direction dD2 as shown in FIG. 4 are calculated with respect to a pixel (x, y) of the intra-cavity image by the following equations (1) to (4).

$$dH(x, y) = P(x, y) - 0.5 \times (P(x-r, y) + P(x+r, y)) \quad (1)$$

$$dV(x, y) = P(x, y) - 0.5 \times (P(x, y-r) + P(x, y+r)) \quad (2)$$

$$dD1(x, y) = P(x, y) - 0.5 \times (P(x-r', y+r') + P(x+r', y-r')),$$
where r' is an integer calculated by rounding off $r/(2^{0.5})$ \quad (3)

$$dD2(x, y) = P(x, y) - 0.5 \times (P(x-r', y-r') + P(x+r', y+r'))$$
where r' is an integer calculated by rounding off $r/(2^{0.5})$ \quad (4)

It should be noted that P(x, y) is a pixel value of coordinates (x, y) of the intra-cavity image and r is a parameter (integer) showing a pixel range in the quadratic differentiation calculation. When the parameter r is set to a small value, an edge component of high frequency can be calculated, and when the parameter r is set to a large value, an edge component of low frequency can be calculated. Here, the parameter r may be set statically in advance or set dynamically based on an image and the like. Alternatively, the parameter r may be configured to be given from an outside and processed.

Next, a maximum value on a plus side of the calculation result of the quadratic differentiation for each direction is calculated by the following equation (5) and is treated as an edge intensity E in the pixel.

$$E(x, y) = \max(0, dH(x, y), dV(x, y), dD1(x, y), dD2(x, y)) \quad (5)$$

Figure 5A:
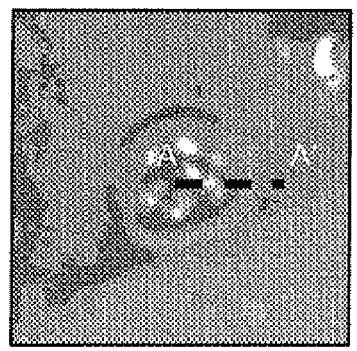
FIG. 5A shows an image example of a bubble part.
Figure 5B:
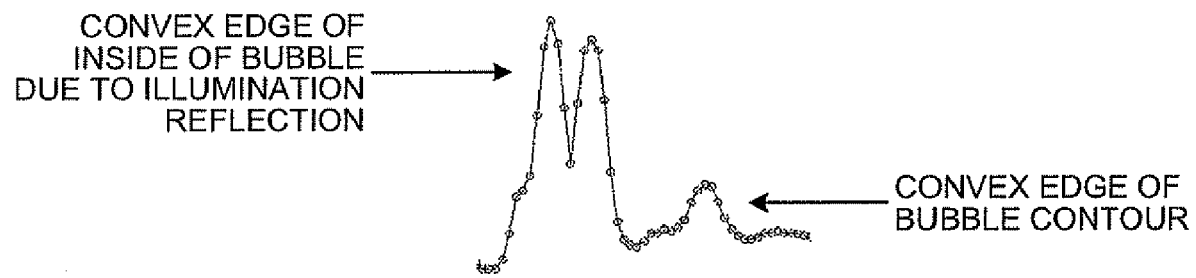
FIG. 5B shows a change in a pixel value of a part along a line A-A' in the image of the bubble part shown in FIG. 5A.
Figure 6:
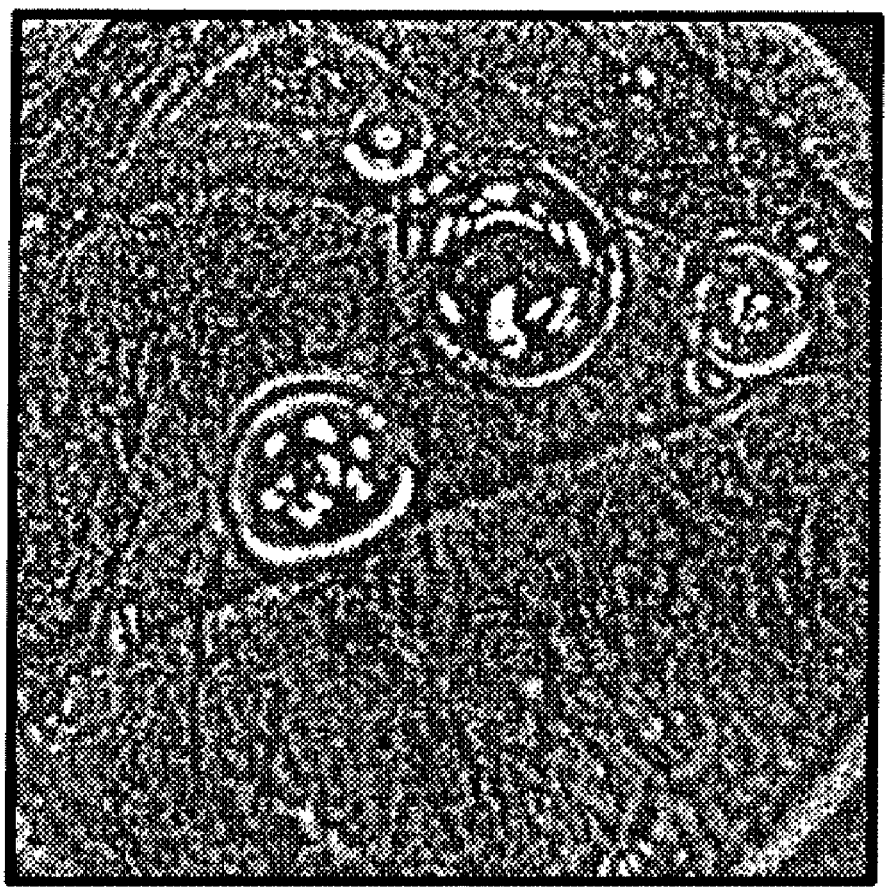
FIG. 6 shows an example of a result of the edge intensity calculation.

By the above described processing, the edge intensity calculation is performed so that an edge intensity is large at a part where a change in a pixel value within the range specified by the parameter r exhibits a convex shape in any one of the horizontal direction, the vertical direction, the first diagonal direction, and the second diagonal direction. A change in a pixel value of a part along a line A-A' in an image of a bubble part shown in FIG. 5A is shown in FIG. 5B. Based on the characteristics, shown in FIG. 5B, of the bubble image, a convex edge due to a reflection of an illumination for imaging is present in a contour part and an inside of the bubble of the intra-cavity image. Therefore, the processing described above enables obtaining an edge intensity which reflects characteristics of a bubble structure while suppressing a change in a pixel value attributed to other structures in a body cavity. A result example of the edge intensity calculation with respect to the intra-cavity image shown in FIG. 2 is shown in FIG. 6.

Though the calculation method of the edge intensity of the intra-cavity image via the quadratic differentiation for each direction is shown so far in the first embodiment, the calculation method of the edge intensity may be modified to any other methods depending on an illumination system and an imaging system for illuminating and capturing the intra-cavity image. For example, the calculation can be performed via a spatial filtering by using already known linear differential filters (the Prewitt filter, the Sobel filter, and the like) and quadratic differentiation filters (the Laplacian filter, the Laplacian of Gaussian (LOG) filter, and the like) (reference: Digital Image Processing; Edge Extraction, Computer Graphic Arts Society, p. 114).

Figure 7:
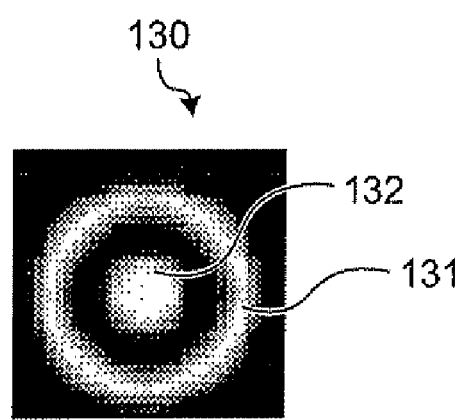
FIG. 7 shows an example of a bubble model.
Figure 8:
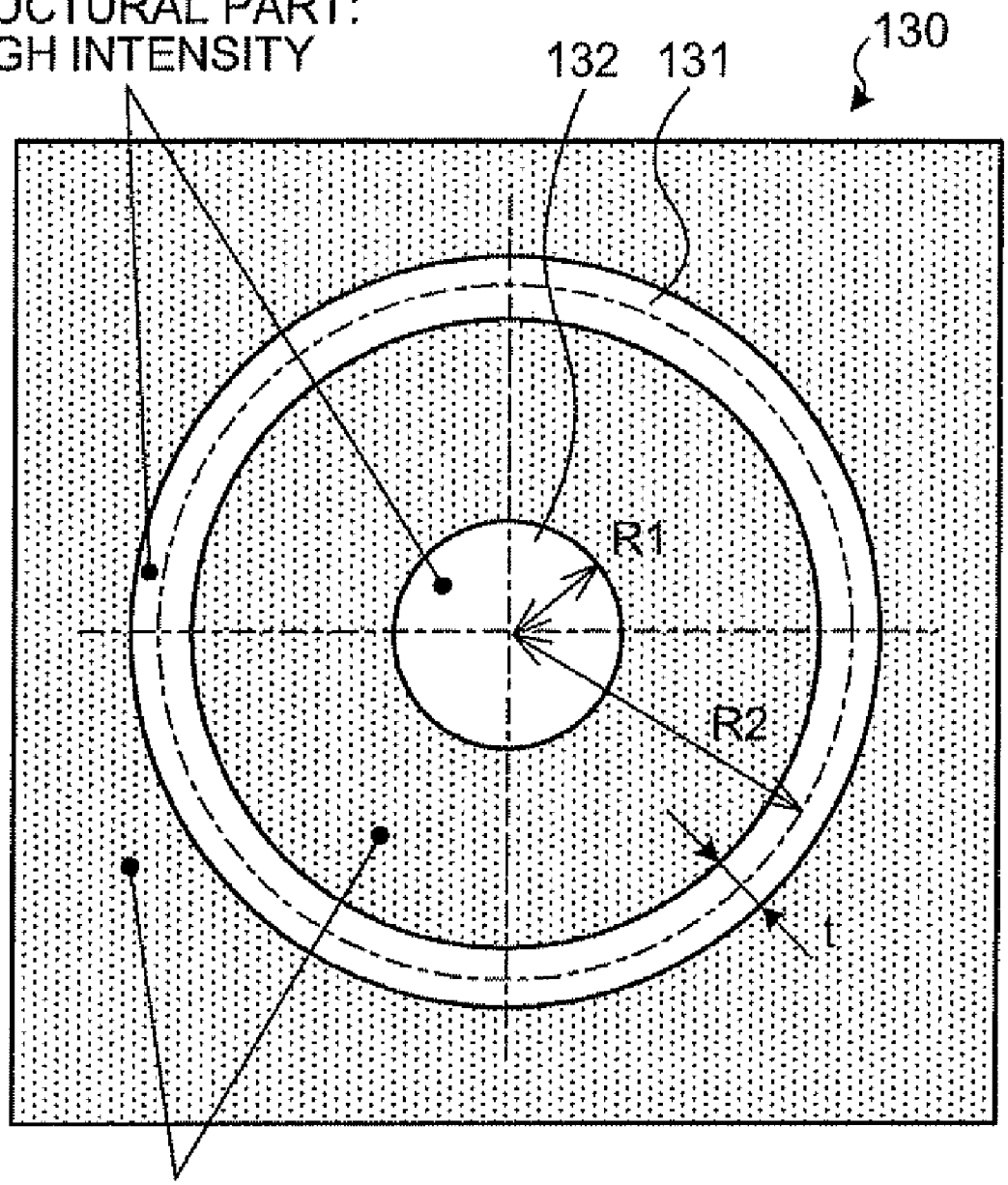
FIG. 8 shows an example of a basic graphic for creating the bubble model.
Figure 9A:
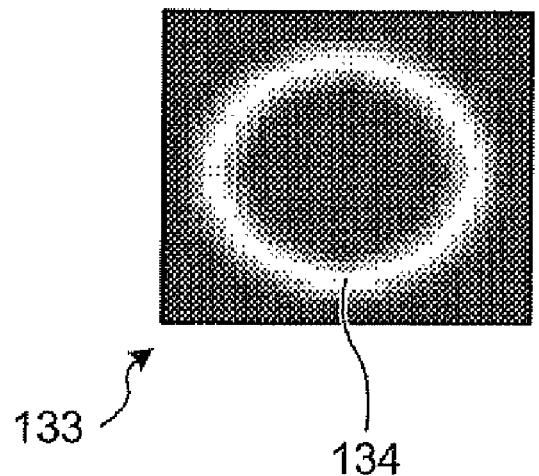
FIG. 9A shows a modification example of the bubble model.
Figure 9B:
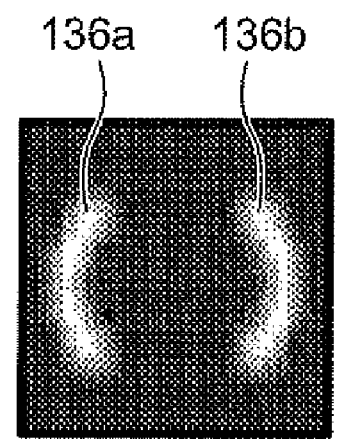
FIG. 9B shows another modification example of the bubble model.
Figure 9C:
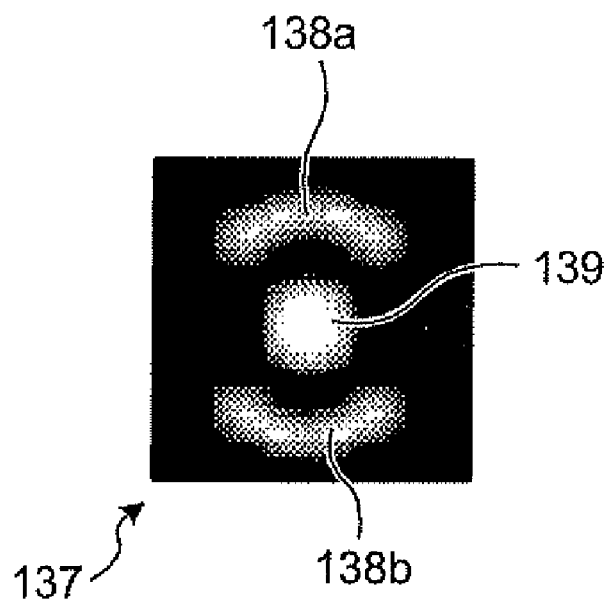
FIG. 9C shows still another modification example of the bubble model.
Figure 9D:
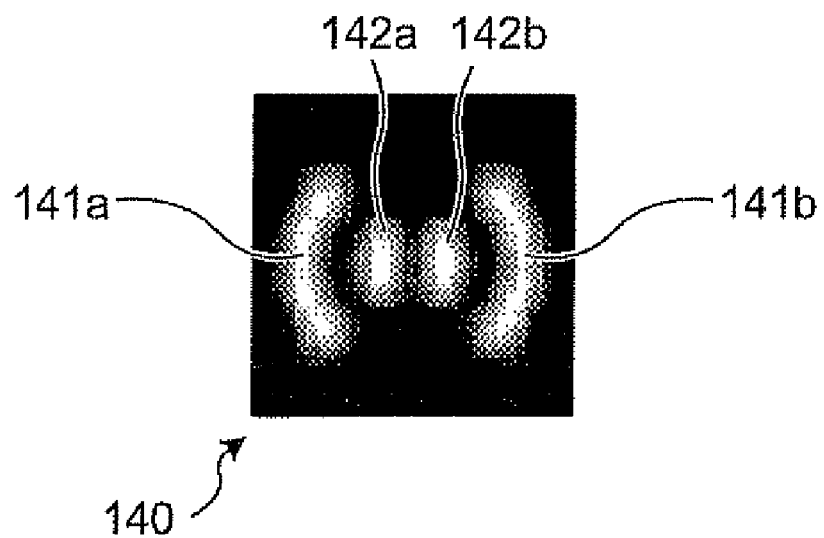
FIG. 9D shows still another modification example of the bubble model.

Next, the correlation value calculator 102 calculates a correlation value between the edge intensity calculated by the edge intensity calculator 101 and a bubble model (step S103). Here, the bubble model is set based on characteristics in a bubble image, for example characteristics of having a convex edge of an arc shape present in a contour part and an inside of the bubble due to a reflection of an illumination in a bubble image in an intra-cavity image obtained by an illumination and imaging system of a capsule endoscope, and is a template pattern having a high intensity structural part 131 of a ring shape and a high intensity structural part 132 positioned in an inside of the ring shape as shown in FIG. 7. Though there are a variety of methods of creating the bubble model, the bubble model can be created by creating a basic graphic constituted by a background part of low intensity and a structural part of high intensity as shown in FIG. 8, and using a smoothing filter (the Gaussian filter and the like) to perform a spatial filtering. Here, a radius R1 and a radius R2 respectively of the high intensity structural parts 131 and 132, and a width t of the high intensity structural part 131 are parameters concerning a graphic size in the example of the basic graphic for creating the bubble model shown in FIG. 8, and may be set statically in advance or set dynamically based on an image and the like. Alternatively, the parameters may be configured to be given from an outside and processed. The same applies to parameters for adjusting a degree of smoothing.

When characteristics of the bubble image in the intra-cavity image to be detected are taken into consideration, it is important for the bubble model to have a high intensity structural part at least having an arc shape since an assembly of arc shapes forms the bubble image, and the bubble model is not limited to such bubble model 130 as shown in FIG. 7 and other bubble models as shown in FIGS. 9A to 9D may be used, for example. A bubble model 133 shown in FIG. 9A has a high intensity structural part 134 of a slightly elliptical and flattened ring shape. A bubble model 135 shown in FIG. 9B has paired high intensity structural parts 136a and 136b each having an arc shape. A bubble model 137 shown in FIG. 9C has paired high intensity structural parts 138a and 138b each having an arc shape, and a high intensity structural part 139 positioned in an inside of the high intensity structural parts 138a and 138b. A bubble model 140 shown in FIG. 9D has paired high intensity structural parts 141a and 141b each having an arc shape, and paired high intensity structural parts 142a and 142b positioned in an inside of the high intensity structural parts 141a and 141b.

Here, the correlation between the edge intensity and the bubble model can be calculated by converting both of the edge intensity and the bubble model into a frequency space via the Fourier transform, and performing the inverse Fourier transform of both products as shown in equation (6).

$$C=F^{-1}\{F\{E\} \times F\{R\{a\}\}\} \quad (6)$$

Here, C indicates a correlation value, E indicates an edge intensity, a indicates a bubble model, $F\{\ \}$ indicates the Fourier transform, $F^{-1}\{\ \}$ indicates the inverse Fourier transform, and $R\{\ \}$ indicates a rotation of 180 degrees.

Figure 10:
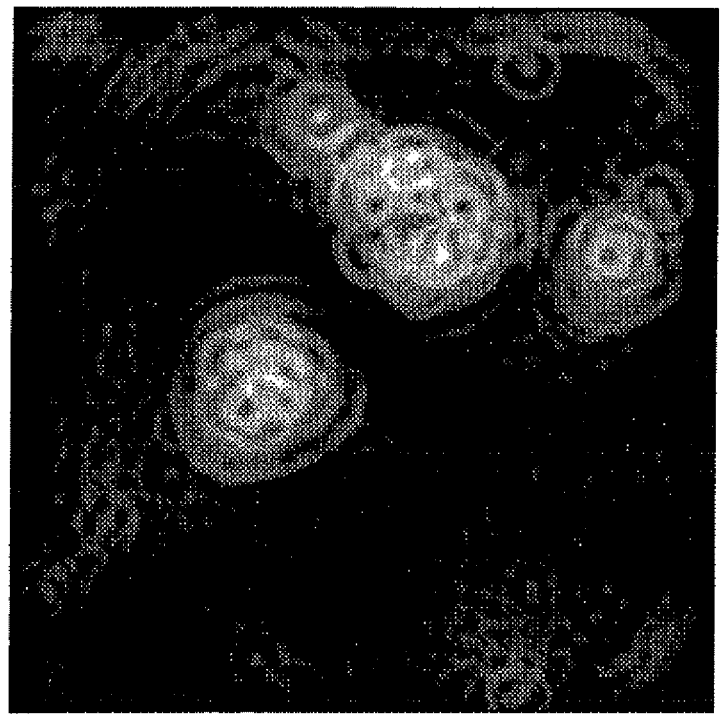
FIG. 10 shows a calculation result of a correlation value between the result example of the edge intensity calculation shown in FIG. 6 and the bubble model shown in FIG. 7.

FIG. 10 shows a calculation result of a correlation value between the result example of the edge intensity calculation shown in FIG. 6 and the bubble model shown in FIG. 7. Since the processing performed by the correlation value calculator 102 is no more and no less than to calculate a similarity between the edge intensity and the bubble model as a correlation value, other methods of calculating a similarity (SAD: Sum of Absolute Differences, SSD: Sum of Squared Differences, and the like) which are already known as a method for a template matching may be utilized (reference: Digital Image Processing; Similarity, Computer Graphic Arts Society, p. 203).

Figure 11:
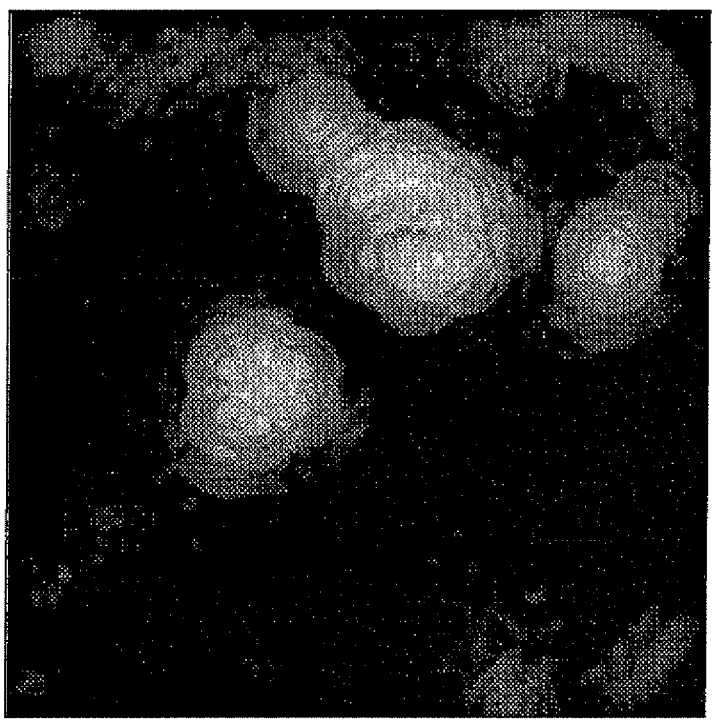
FIG. 11 shows an example of a calculation result of a correlation value obtained by using plural kinds of bubble models with respect to the result example of the edge intensity calculation shown in FIG. 6.

Besides, though the example of obtaining a correlation with one bubble model is shown in the first embodiment, it is possible to deal with a greater variety of bubbles by setting in advance plural kinds of bubble models whose size and shape are different, and obtaining a maximum correlation value for each pixel position after obtaining a correlation value between the edge intensity and each bubble model. FIG. 11 shows a result example of the correlation value calculation by using plural kinds of bubble models with respect to the result example of the edge intensity calculation shown in FIG. 6.

Figure 12:
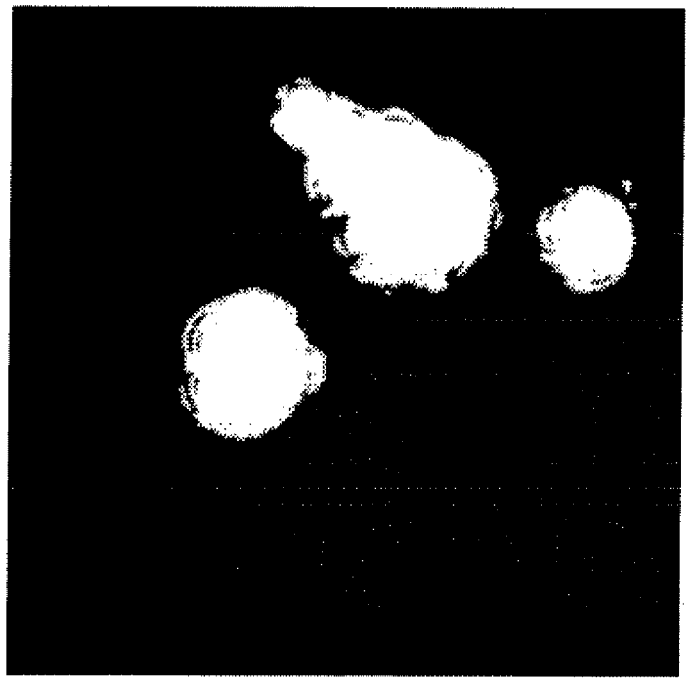
FIG. 12 shows a detection result of a bubble area based on the correlation value.

Next, the bubble area detector 103 detects a bubble area in the intra-cavity image based on the correlation value calculated by the correlation value calculator 102 (step S104). A part which exhibits a high correlation with the bubble model showing characteristics of a bubble has high possibility of being ascribed to a bubble area. So, the bubble area detector 103 sets a predetermined threshold value and detects a part having a correlation value higher than the threshold value as a bubble area in the intra-cavity image. FIG. 12 shows a bubble area detection result based on the correlation value, an outline on a colored background being a part detected as a bubble area.

Finally, the calculation unit 110 outputs information of the bubble area detected by the bubble area detector 103 (step S105) and the processing in the image processing apparatus 100 ends.

In the image processing apparatus 100 according to the first embodiment described above, a bubble area in an intra-cavity image can be detected properly thanks to a configuration in which an edge intensity of a pixel in the intra-cavity image is calculated, a correlation value between the calculated edge intensity and a bubble model which is set in advance based on characteristics of a bubble image, and a bubble area in the intra-cavity image is detected based on the calculated correlation value. Thus, a deterioration in accuracy of an organ determination and a diseased site detection in the intra-cavity image can be suppressed by eliminating, as an invalid pixel, a pixel of the bubble area in the intra-cavity image captured by a capsule endoscope and the like from a subsequent image processing.

Figure 13:
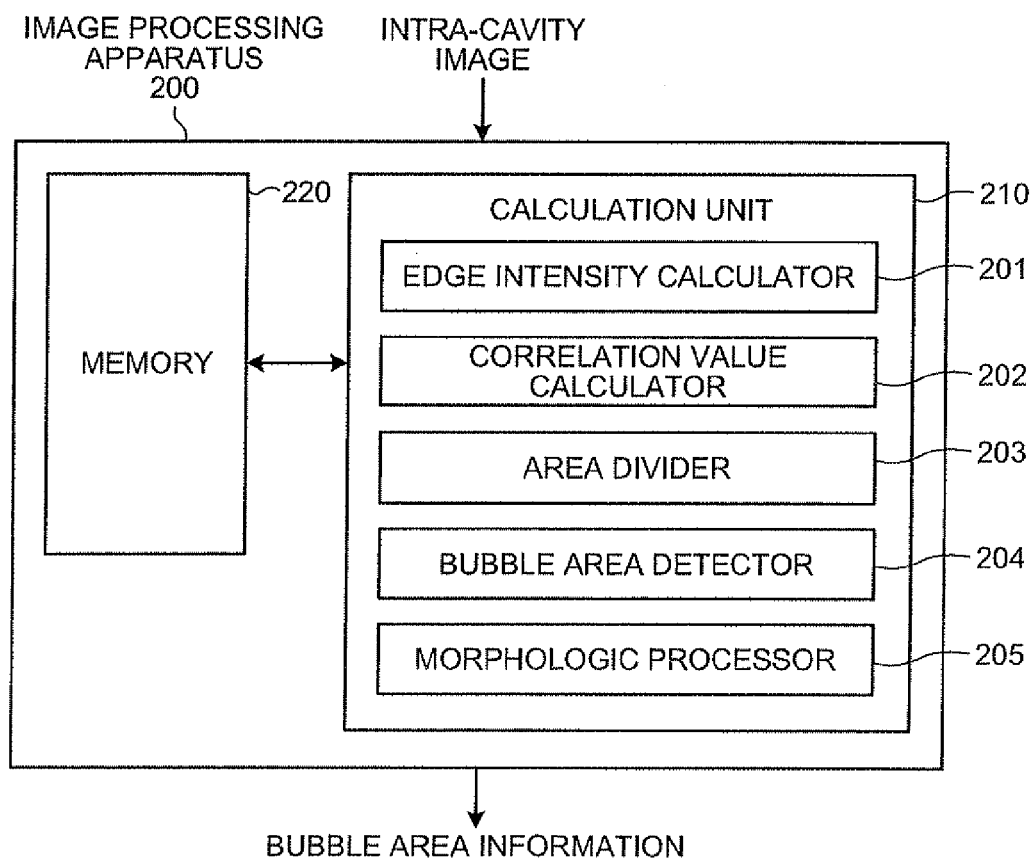
FIG. 13 is a schematic block diagram of a structure of an image processing apparatus according to a second embodiment of the present invention.

A second embodiment will be explained next. FIG. 13 is a schematic block diagram of a structure of an image processing apparatus according to the second embodiment of the present invention. An image processing apparatus 200 according to the second embodiment includes: a calculation unit 210 which is constructed by a microcomputer and has an edge intensity calculator 201 and a correlation value calculator 202 respectively having the same functions as the edge intensity calculator 101 and the correlation value calculator 102 in the image processing apparatus 100 according to the first embodiment, an area divider 203 that divides an intra-cavity image into areas based on an edge in the intra-cavity image, a bubble area detector 204 that detects a bubble area in the intra-cavity image based on the correlation value calculated by the correlation value calculator 202 and the result of the area division performed by the area divider 203, and a morphologic processor 205 that performs a morphologic processing with respect to the result of the bubble area detection performed by the bubble area detector 204; and a memory 220 which stores obtained intra-cavity images and data used by each part. As for a configuration for inputting intra-cavity images as a processing subject into the image processing apparatus 200 and a configuration for processing the result of the bubble area detection after the result is output, no specific limitation is set in the embodiment similarly to the first embodiment.

Figure 14:
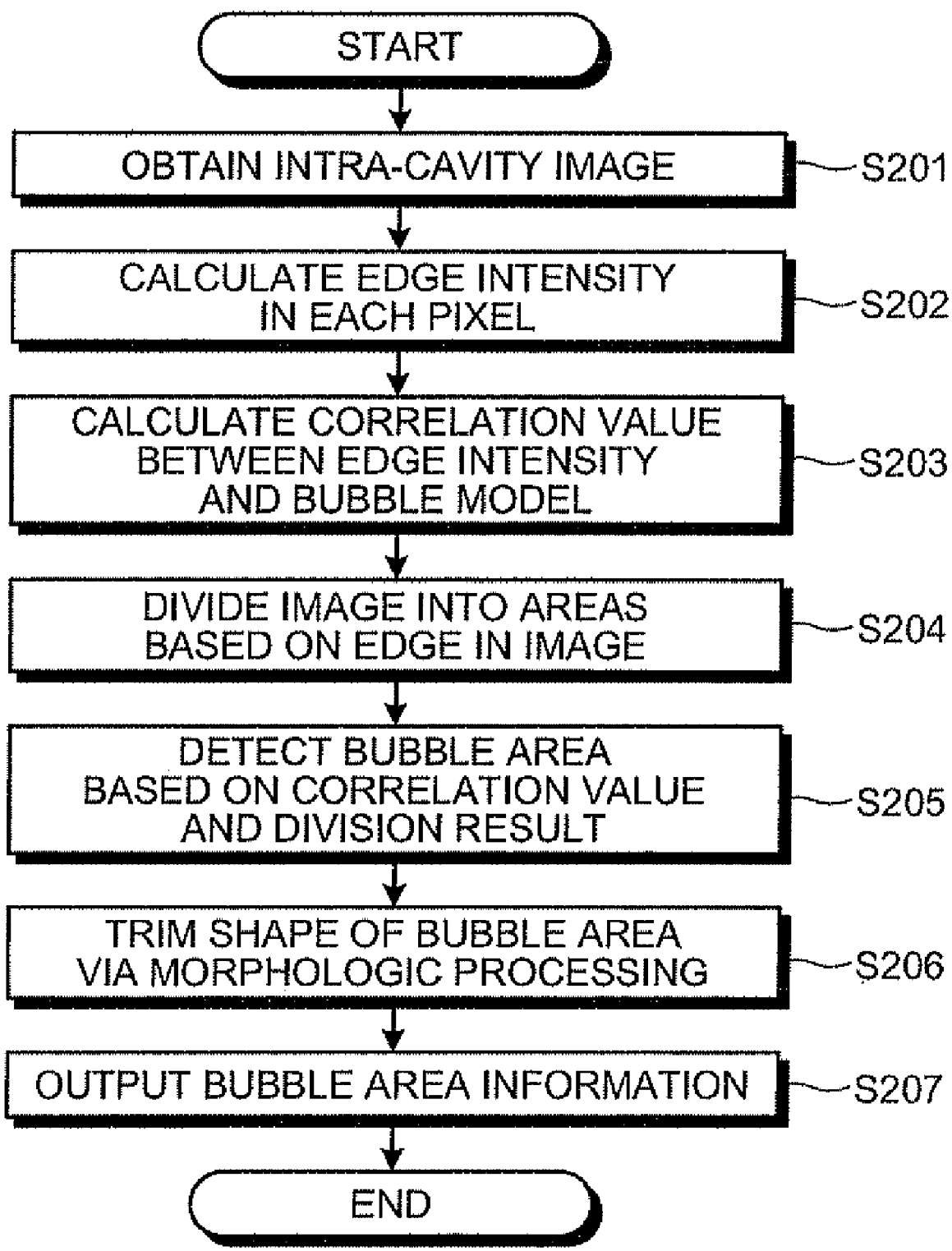
FIG. 14 is a schematic flowchart of a processing executed by a calculation unit of the image processing apparatus according to the second embodiment.

FIG. 14 is a schematic flowchart of a processing executed by the calculation unit 210 of the image processing apparatus 200 according to the second embodiment. It should be noted that processing steps S201 to S203 are the same as the processing steps S101 to S103 in the first embodiment. Processing steps S204 to S207 will be explained below in contrast with the structure shown in FIG. 13.

Figure 15:
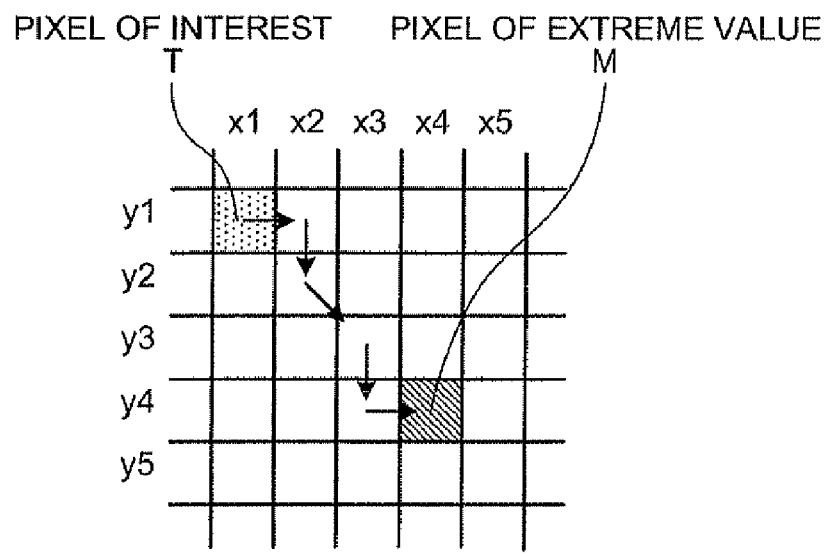
FIG. 15 is a view showing an example of scanning from a given pixel of interest T shown by coordinates (x1, y1) to a pixel of extreme value M shown by coordinates (x4, y4)
Figure 16:
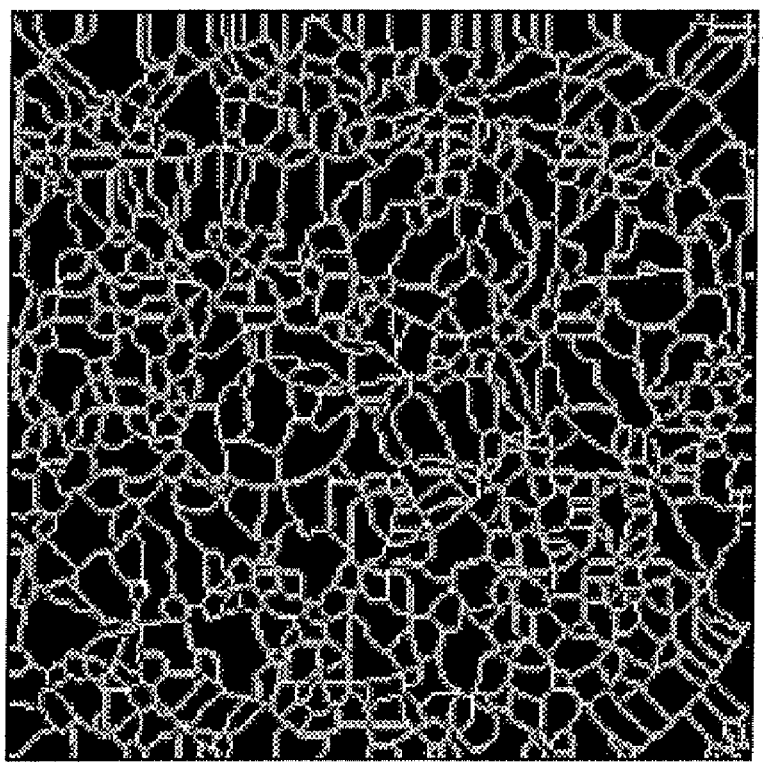
FIG. 16 shows an example of a result of performing an area division with respect to the intra-cavity image shown in FIG. 2 by using an area divider.

The area divider 203 divides the intra-cavity image into areas based on an edge in the intra-cavity image (step 3204). As an area division method, a technique disclosed in International Publication No. WO2006/080239 by the same applicant as the present invention is used. First of all as a procedure, a gradient direction of a pixel value of each pixel is calculated after a smoothing processing for the purpose of eliminating a noise is performed with respect to the intra-cavity image. Here, the gradient direction is a direction in which an intensity difference with a neighborhood pixel is the smallest (a direction of the largest subtractive value). Next, a pixel of extreme value to be reached along the gradient direction of a pixel value of each pixel is calculated and the image is divided into areas so that all the pixels to the proximate pixel of extreme value are zoned as a same area. FIG. 15 is a view showing an example of scanning from a given pixel of interest T shown by coordinates (x1, y1) to a pixel of extreme value M shown by coordinates (x4, y4). FIG. 16 shows an example of a result of performing the area division with respect to the intra-cavity image shown in FIG. 2 by using the area divider 203.

As another area division method, a method of using a watershed algorithm is also available, for example (reference: Luc Vincent and Pierre Soille, Watersheds in digital spaces: An efficient algorithm based on immersion simulations, Transactions on Pattern Analysis and Machine Intelligence, Vol. 13, No. 6, pp. 583-598, June 1991). The watershed algorithm is a method of dividing an image so that, when a geography in which pixel value information of the image is expressed by an altitude is filled with water, a boundary is formed between different water hollows. By applying the watershed algorithm after performing a proper smoothing with respect to the intra-cavity image, a result of area division similar to the result shown in FIG. 16 can be obtained.

Figure 17:
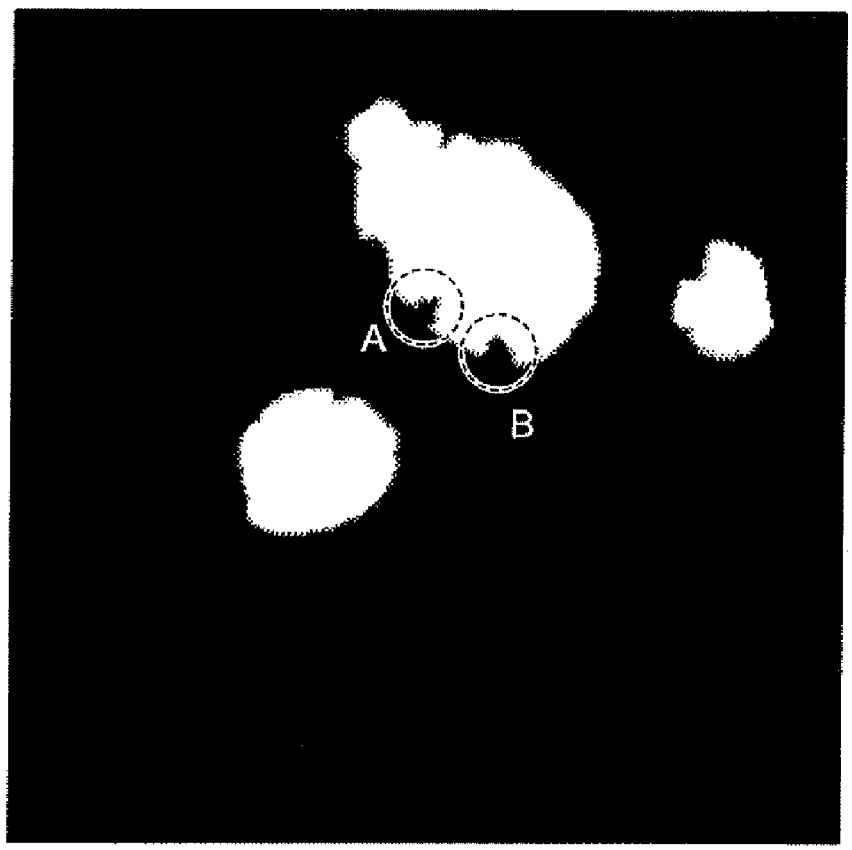
FIG. 17 shows a result of detection by a bubble area detector.

Next, the bubble area detector 204 detects a bubble area in the intra-cavity image based on the correlation value calculated by the correlation value calculator 202 and the result of the area division performed by the area divider 203 (step S205). In fact, the bubble area detector 204 first obtains an average value of correlation values for each area in the area division result. Since a correlation value obtained in an area ascribed to the bubble area is high, the bubble area detector 204 sets a predetermined threshold value and detects as the bubble area an area whose average correlation value is higher than the threshold value. FIG. 17 shows the result of the detection by the bubble area detector 204. As seen from FIG. 17, it is possible to obtain a boundary of the bubble area more accurately with correspondence to a contour edge of a bubble in the intra-cavity image by using the result of the area division performed by the area divider 203.

Here, there is a case where a proper boundary cannot be partially obtained due to an influence of a noise and the like, as shown at parts A and B in FIG. 17. Besides, there is a case where a foramen or a minute area which is not a bubble area is present inside the bubble area, like the result of the bubble area detection shown in FIG. 12 in the first embodiment. Then, the morphologic processor 205 trims an irregularity in shape of the bubble area due to such noises via a morphologic processing (step S206) (reference: Hidefumi KOBATAKE, Mathematic Morphology, CORONA PUBLISHING CO., LTC.). A basic of the morphologic processing is two processings i.e., dilation and erosion, and an object area is processed by using a basic graphic (reference image) called a structural element in each processing. A content of each processing is as follows.

Figure 18:
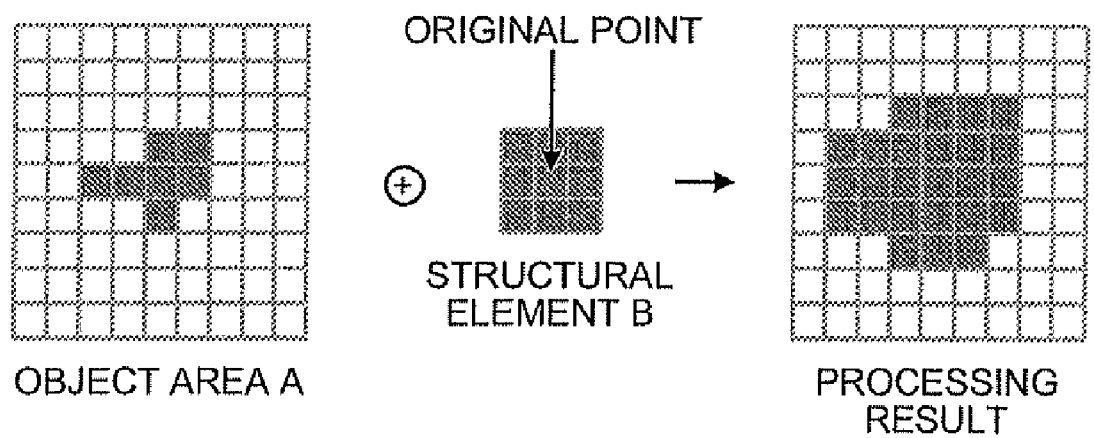
FIG. 18 is a view showing a dilation processing.

Dilation: to output an area covered by a structural element B at a time of parallel translation of an original point of the structural element B in an object area A (see FIG. 18).

Figure 19:
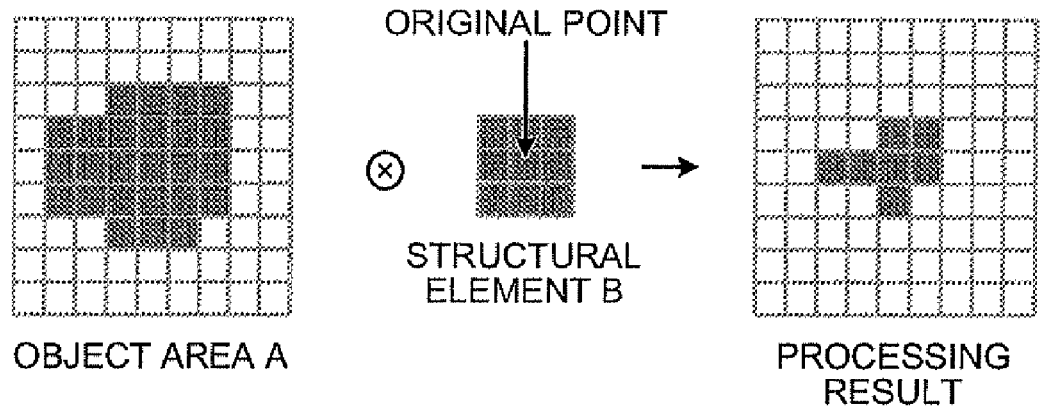
FIG. 19 is a view showing an erosion processing.

Erosion: to output an area covered by an original point of a structural element B at a time of parallel translation of the structural element B in an object area A (see FIG. 19).

Figure 20:
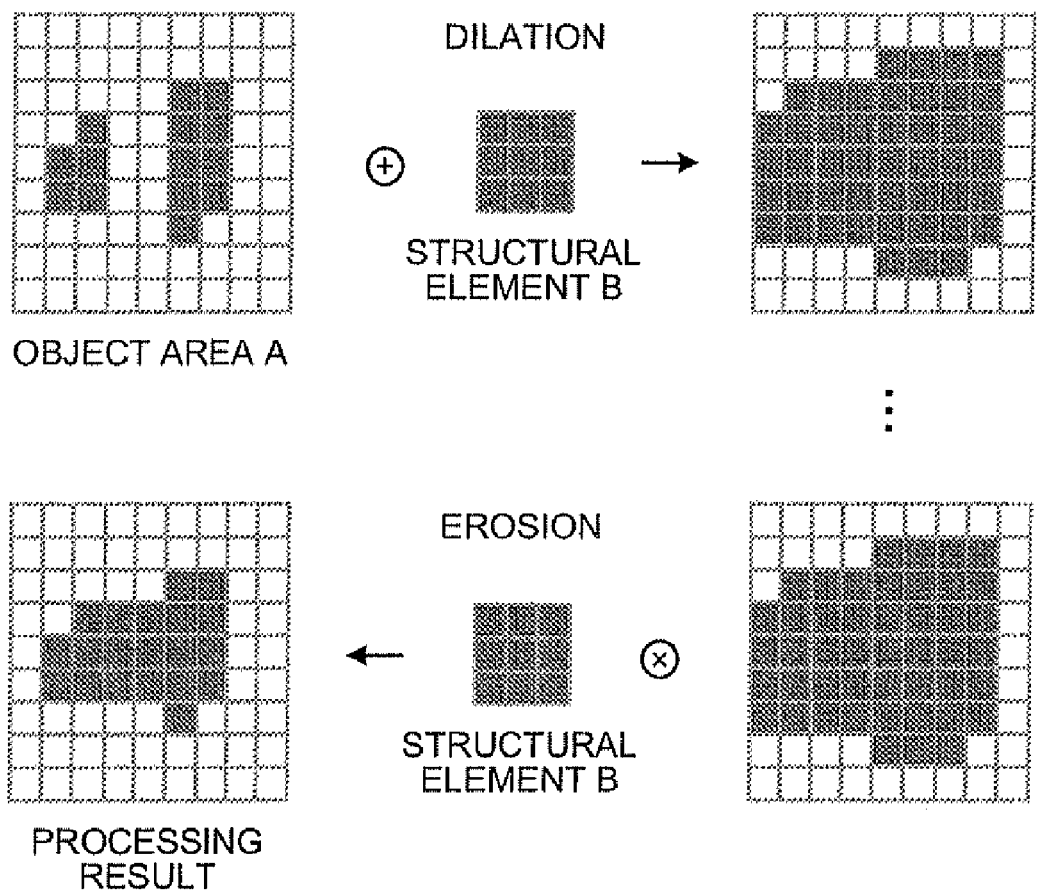
FIG. 20 is a view showing a closing processing.

As a processing formed by a combination of the two processings, a closing (to perform the erosion after the dilation with respect to an object area: see FIG. 20) and an opening (to perform the dilation after the erosion with respect to an object area) are available. Accordingly, a content of each processing is as follows.

Closing: to output an area surrounded by a structural element B at a time of translation of the structural element B circumscribing an outside of an object area A (see FIG. 20).

Opening: to output an area surrounded by a structural element B at a time of translation of the structural element B inscribing an inside of an object area A.

Figure 21:
FIG. 21 shows an example of a result of performing the closing processing with respect to the result of the bubble area detection shown in FIG. 17 by using a circular structural element.

By performing these processings with respect to the detected bubble area, an irregularity in shape can be trimmed. FIG. 21 shows an example of a result of performing the closing processing with respect to the detection result of the bubble area shown in FIG. 17 by using a circular structural element, and a state of trimmed shapes of parts A and B in FIG. 17 can be seen. The morphologic processor 205 performs various morphologic processings depending on an intended use in a way of performing the closing processing for eliminating a foramen in a bubble area; the opening processing for eliminating, except for a bubble area, an area having a minute noise; and the dilation processing for obtaining an area slightly wider than the detected bubble area.

Finally, the calculation unit 210 outputs information of the trimmed bubble area (step S207) and the processing in the image processing apparatus 200 ends.

In the image processing apparatus 200 according to the second embodiment described above, since a bubble area in an image is detected based on, in addition to the correlation value between the calculated edge intensity and the bubble model, the result of dividing the image into areas based on an edge in the intra-cavity image, more accurate detection, with a correspondence to a contour edge of a bubble, of the bubble area can be realized. Thus, even in a case where the bubble area is present in the vicinity of a diseased site, the image processing apparatus 200 can be made good use of for more properly detecting a diseased site and the like without detecting the diseased site inclusively as the bubble area.

The processing procedure shown in FIGS. 3, 14, and the like performed by each of the edge intensity calculators 101 and 201, the correlation value calculators 102 and 202, the area divider 203, the bubble area detectors 103 and 204, and the morphologic processor 205 may be realized by making an image processing apparatus constructed by a computer such as a personal computer execute prepared image processing program. The image processing program can be distributed via a network such as the Internet. Besides, the image processing program can be recorded in a recording medium such as a hard disk drive, a floppy disk, a compact disk read only memory, a magnetic disk, and a digital versatile disk which can be read by a computer, and executed by being read out from the recording medium by the computer.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus, comprising:
   an edge intensity calculator which calculates an edge intensity of a pixel in an image;
   a correlation value calculator which calculates a correlation value between the calculated edge intensity and a bubble model set in advance based on characteristics of a bubble image; and
   a bubble area detector which detects a bubble area based on the calculated correlation value.

2. The image processing apparatus according to claim 1, wherein
   the correlation value calculator calculates correlation values with plural kinds of bubble models, and
   the bubble area detector detects the bubble area based on the correlation values calculated with the plural kinds of bubble models.

3. The image processing apparatus according to claim 1, further comprising an area divider which divides the image into areas based on an edge in the image, wherein
   the bubble area detector detects the bubble area based on the correlation value and a result of the area division.

4. The image processing apparatus according to claim 1, wherein the bubble model is a template pattern having a high intensity structural part of an arc shape.

5. The image processing apparatus according to claim 1, wherein the bubble model is a template pattern having a high intensity structural part of a ring shape.

6. The image processing apparatus according to claim 1, wherein the bubble model is a template pattern having a high intensity structural part of a ring shape and another high intensity structural part positioned inside the ring shape.

7. The image processing apparatus according to claim 1, wherein the edge intensity calculator uses a processing of a quadratic differentiation for each direction to calculate the edge intensity.

8. The image processing apparatus according to claim 1, further comprising a morphologic processor which performs a morphologic processing with respect to a detection result of the bubble area detector.

9. The image processing apparatus according to claim 1, wherein the image is an image captured in a body cavity.

10. An image processing program product having a computer readable medium including programmed instructions for detecting a bubble area in an image, wherein the instructions, when executed by an image processing apparatus, cause the image processing apparatus to perform:
    calculating an edge intensity of a pixel in an image;
    calculating a correlation value between the calculated edge intensity and a bubble model set in advance based on characteristics of a bubble image; and
    detecting a bubble area based on the calculated correlation value.

11. The image processing program product according to claim 10, wherein
    correlation values are calculated with plural kinds of bubble models in the calculating, and
    the bubble area is detected based on the correlation values calculated with the plural kinds of bubble models in the detecting.

12. The image processing program product according to claim 10, wherein the instructions further cause the image processing apparatus to execute dividing the image into areas based on an edge in the image, and wherein
    the bubble area is detected based on the correlation value and a result of the area division in the detecting.

13. The image processing program product according to claim 10, wherein the bubble model used for calculating the correlation value is a template pattern having a high intensity structural part of an arc shape.

14. The image processing program product according to claim 10, wherein the bubble model used for calculating the correlation value is a template pattern having a high intensity structural part of a ring shape.

15. The image processing program product according to claim 10, wherein the bubble model used for calculating the correlation value is a template pattern having a high intensity structural part of a ring shape and another high intensity structural part positioned inside the ring shape.

16. The image processing program product according to claim 10, wherein a processing of a quadratic differentiation for each direction is used to calculate the edge intensity in the calculating.

17. The image processing program product according to claim 10, wherein the instructions further cause the image processing apparatus to execute performing a morphologic processing with respect to a detection result of the bubble area detecting.

18. The image processing program product according to claim 10, wherein the image is an image captured in a body cavity.

19. An image processing method, comprising:
    calculating an edge intensity of a pixel in an image;
    calculating a correlation value between the calculated edge intensity and a bubble model set in advance based on characteristics of a bubble image; and
    detecting a bubble area based on the calculated correlation value.

* * * * *